United States Patent [19] [11] 4,166,900
Heimsch et al. [45] Sep. 4, 1979

[54] PREPARATION OF REFINED OLEFIN/MALEIC ACID COPOLYMERS

[75] Inventors: Robert A. Heimsch, St. Louis; John H. Johnson, Kirkwood, both of Mo.

[73] Assignee: Monsanto Company, St. Louis, Mo.

[21] Appl. No.: 863,759

[22] Filed: Dec. 23, 1977

[51] Int. Cl.² ............... C08F 6/12; C08F 222/02; A61K 31/19
[52] U.S. Cl. .................... 528/491; 424/78; 526/317
[58] Field of Search ............ 526/272, 317; 528/491; 424/78

[56] References Cited

U.S. PATENT DOCUMENTS

| | | | |
|---|---|---|---|
| 3,560,457 | 2/1971 | Hazen et al. | 526/272 |
| 3,729,450 | 4/1973 | Galiano et al. | 526/272 |
| 3,729,451 | 4/1973 | Blecke et al. | 526/272 |

Primary Examiner—John Kight, III
Attorney, Agent, or Firm—Joseph D. Kennedy; James W. Williams, Jr.

[57] ABSTRACT

Olefin/maleic acid copolymer is refined to pharmaceutical quality by use of dichloroethane to remove contaminants, as by precipitating from solution with dichloroethane.

19 Claims, No Drawings

PREPARATION OF REFINED OLEFIN/MALEIC ACID COPOLYMERS

The present invention concerns a method of isolating and purifying olefin/maleic acid copolymers and is particularly concerned with use of dichloroethane to effect fractional precipitation from solution of a higher olefin copolymer. The polymers are provided in a form substantially free from low molecular weight materials and suitable for medicinal use.

BACKGROUND OF THE INVENTION

Olefin/maleic acid copolymers have been shown effective as agents for controlling blood cholesterol levels as described in Fields and Johnsons U.S. Pat. No. 3,923,972 issued Dec. 2, 1975. Olefin/maleic copolymers can be prepared in the anhydride form by the polymerization methods described in the aforesaid patent or in the patents there cited, for example, Fields and Johnson U.S. Pat. No. 3,340,680. Such polymerization methods frequently utilize a solvent for the reaction which dissolves the monomers, but not the resulting copolymer, so that the copolymer precipitates. This is an effective method of preparing and isolating polymer for normal industrial uses, although with higher olefins it may be difficult to obtain the polymer in readily filterable form. However polymer obtained in such procedures generally contains substantial amounts of residual monomers and low molecular weight polymer materials. A Hazen and Heilman U.S. Pat. No. 3,560,456 describes a method in which a copolymer of maleic anhydride and an olefin of 16 to 18 carbon atoms is precipitated from solution by propyl alcohol in order to have the polymer in particular form for filtration. The procedure is useful but the product still contains substantial amounts of low molecular weight materials and some residual amounts of esterified polymer. The product obtained by the described procedure can, if desired, be utilized for further refinement in accord with the present invention.

SUMMARY OF THE INVENTION

The present invention involves a procedure for refining olefin/maleic acid copolymer by precipitating same from solution with chemically inert 1,2-dichloroethane. The invention also concerns a procedure for refining the copolymers by washing with 1,2-dichloroethane. The invention is also concerned with the process for hydrolyzing olefin/maleic anhydride copolymers, followed by various solution-precipitation, filtration, washing, hydrolysis and drying steps to obtain refined olefin/maleic acid copolymer, and with the refined product.

DETAILED DESCRIPTION OF THE INVENTION

Olefin/maleic copolymer polymerization product generally contains residual monomers and some low molecular weight fractions. It is desirable to remove those materials from product intended for medicinal use. While olefin/maleic acid copolymers as a class have some useful properties in common and are of interest in the present invention, the higher olefin/maleic acid copolymers are of particular interest. The higher olefins have a longer hydrocarbon chain and tend to give the copolymers more lipophilic properties, making them more useful as agents to control blood cholesterol levels. The hydrocarbon chain also influences solubility properties and effectiveness of refinement procedures as described herein. The copolymers of particular interest herein will generally be of olefins of at least 8 carbon atoms, often of about 10 to about 22 or more carbon atoms. The procedures herein are particularly directed for use with such copolymers of such olefins with maleic acid. While various derivatives of the maleic moiety are known and may be useful, the acid form has properties especially appropriate for the solvent-precipitation procedures herein. The acid form can conveniently be obtained by hydrolysis of the anhydride form, but other methods of obtaining the olefin/maleic acid copolymer for use herein can be employed. It will be recognized, of course, that high molecular weight polymers are not generally completely homogeneous materials, and may vary somewhat in functional groups, as well as in structure and molecular weight. The acid form of the copolymer exhibits a tendency to convert to the anhydride, and the copolymers utilized herein, as well as the refined product, generally contain small amounts of maleic anhydride moiety, which may range up to 20 to 25% or so of the maleic moieties in the polymer. It will generally be preferred to work with and produce product with about 5 to 10% or so anhydride content.

The procedures herein are intended primarily for removal of low molecular weight polymers, residual olefin or maleic monomer, or other non-polymeric material. In medicinal use, the low molecular weight or monomeric materials could have a different physiological effect than high molecular weight polymer. The high molecular weight polymer is non-systemic when administered orally, i.e., not absorbed from the gastrointestinal tract. The degree of absorbability of the monomers and low molecular weight polymers have not been determined precisely, and no limits have been established for their presence in pharmaceutical grade polymer. However, the procedures described herein produce polymer which is acceptable from a toxicity standpoint in animal tests. The monomer content can be reduced to the parts per million range, such as less than 500 ppm, and often much lower, e.g. less than 10 ppm maleic acid, and the low molecular weight polymers can be reduced to circa no more than 0.1% by weight below molecular weight of 2000 as measured by gel permeation chromatography, or even less if desired.

The $\alpha$-olefin/maleic acid copolymers utilized in and refined by the present invention are insoluble in 1,2-dichloroethane, under normal temperature conditions. However the dichloroethane serves well as a precipitating medium, and is used to precipitate the polymers from solution while some of the low molecular weight or monomeric materials in the crude polymer remain in solution. Dichloroethane has sufficient solubilizing effect on such materials that they are not generally precipitated from solution by addition of dichloroethane.

The present invention involves a selective precipitation of polymer from solution. The polymers are soluble in a number of solvents and the resulting solutions are in general satisfactory for use herein if addition of dichloethane will cause precipitation of the polymer. Of course the precipitation is to be selective in order to effect removal of undesired materials, but this is generally the case if precipitation occurs. It will be recognized that the solvents will vary somewhat in results obtained with respect to polymer recovery vs contaminant removal. However a number of solvents will give similar and satisfactory results, and concentrations of the polymer and the relative amount of dichloroethane can also be varied to give the desired separation. In general some separation has been achieved if the polymer recovered is somewhat less than that placed in solution. Of course the desirable recovery will vary with the amount of contaminant in the orignial polymer. If only a relatively low amount of polymer is recovered, the separation will generally be good, while the efficiency is less than desirable. Of course, additional steps can be taken to recover additional polymer. It will also be recognized that in general multi-stage solution and precipitation procedures can be used if desired to achieve a high degree of separation.

While there is emphasis herein on procedures for precipitation of polymer from solution, it is also an aspect of the invention that dichloroethane can be used to wash or dissolve contaminating materials from the olefin/maleic acid copolymer, either in conjunction with or separately from precipitation procedures. When a system is provided in which the solid polymer is in contact with dichloroethane liquid, the removal of the liquid will carry some dissolved materials therewith. Thus slurry, washing, extraction, and filtration procedures can be used.

One of the main aspects of the present invention is the fact that dichloroethane is a good precipitating solvent for use in refining olefin/maleic acid copolymer. It is sufficiently effective as a non-solvent for the polymer as to cause it to precipitate from most solutions thereof very readily. Nevertheless dichloroethane is an effective solvent for a number of materials, and ordinarily does not cause precipitation from solution of contaminants such as low-molecular weight polymer and monomeric constituents.

Various solvents can be used to place the polymer in solution, but it will generally be desirable to employ a fairly good solvent for the polymer. The polymer can be used in the solutions from relatively low amounts such as 10% or so, up to about the maximum amount which can be employed without the viscosity becoming too excessive for convenient handling, but ordinarily it will be most convenient to operate with polymer concentration of about 30% to about 60% or so by weight in solution, often about 40% to 50% or so, or in the neighborhood of 50%. The amount of precipitating solvent can also be varied, but is often in the range of about 3 to about 12 parts by weight of dichloroethane per part by weight of polymer solution, whether acetone, for example, or other solvent is used in the solution, and is preferably around 6 parts when acetone is the solvent, but these ranges can be varied or extended depending on time, temperature, polymer concentration, or variations in procedure. With a polymer concentration of around 50%, the dichloroethane to solvent ratio in the aforesaid ranges is about 6 to 24 parts dichloroethane to part solvent, and this is illustrative of usual ranges, and, for example, a 12:1 dichloroethane to acetone ratio may be used as a wash solution.

The precipitation of the polymer in the present process occurs upon mixing the polymer solution with dichloroethane, generally by adding the polymer solution to excess dichloroethane. After the polymer has precipitated, a two phase system is present in which solid polymer is in contact with a liquid comprising dichloroethane and a solvent for the polymer. The liquid also comprises contaminants to be removed such as low molecular weight or monomeric impurities. Solvents for the polymer which form such a system with the polymer and dichloroethane are satisfactory. The recovery of polymer will vary with different solvents, and to some extent, of course, with the amount of contaminants in the polymer. However, it will generally be desirable to obtain recoveries of better than 80% or so, and this is feasible with a number of solvents, as determined with 50% polymer solutions, and employing 1,2-dichloroethane in a 12:1 ratio to the solvent. In commercial practice it will be desirable to achieve a fairly high recovery, as high as feasible when balanced with the desired separation and economic factors in the process.

Following the precipitation, the solid polymer is separated from the liquid by usual liquid-solid separation procedures, such as filtration, centrifugation, etc. The contaminants are retained in the liquid, comprised of the dichloroethane and other solvent, while the solid is the polymer product. The polymer may be further washed or otherwise treated as described herein.

A number of solvents are suitable for use herein in conjunction with dichloroethane, including various ketones, ethers, esters, particularly aliphatic esters, aromatic hydrocarbons, etc., for example, acetone, methyl ethyl ketone, methyl isobutyl ketone, cyclohexanone, diisopropyl ether, toluene, xylene, and chloroform. Tetrahydrofuran can also be used, although it has a tendency to cause gel formation.

The polymer as obtained from usual polymerization and recovery procedures may contain 3 to 5% or so by weight olefin monomer. This can be reduced to less than about 0.5% by slurrying or washing the hydrolyzed polymer with 1,2-dichloroethane and separating the polymer from the dichloroethane. The polymer is then further refined by precipitation from solution as described herein.

EXAMPLE 1

An octadecene-1/maleic acid copolymer (hydrolyzed octadecene-1/maleic anhydride copolymer) was employed for solubility determinations. One gram samples of polymer were placed in test tubes, 5 ml. solvent was added, stirred, and let stand for over 48 hours. Results were as follows:

| Solvent | Result |
| --- | --- |
| tetrahydrofuran | soluble |
| methyl ethyl ketone | soluble |
| toluene | viscous solution; (soluble 10 ml) |
| methyl alcohol | sludge which settled |
| isopropyl alcohol | soluble |
| hexane | insoluble |
| petroleum ether | insoluble |

EXAMPLE 2

In solubility determinations, the octadecene-1/maleic acid copolymer was soluble to form 40% by weight solutions in acetone, isopropyl alcohol and ethanol. Solutions of the polymer in several solvents were prepared, and the effectiveness of several non-solvents for precipitation was tested, with results as follows. The separated polymer is that obtained after filtration and drying, and the filtrate residue was obtained by evaporating the filtrate.

| Solution | | | Polymer | Filtrate |
|---|---|---|---|---|
| Amount (grams) | Solvent, Concentration | Non-solvent, ml. | Separated (grams) | Residue (grams) |
| 10 | 40%, isopropanol | 40 ethylene dichloride | 0 | 4 |
| 10 | 40%, acetone | 40 ethylene dichloride | 3.8 | 0.1 |
| 10 | 40%, acetone | 40 propylene dichloride | 0 | 4 |
| 10 | 40%, acetone | 80 ethylene dichloride | 3.4 | 0.3 |
| 10 | 40%, isopropanol | 40 hexane | 0 | 4 |
| 20 | 20%, ethyl acetate | 80 ethylene dichloride | 3.4 | 0.2 |
| 10 | 40%, ethyl acetate | 80 hexane | phase separation | |

The ethylene dichloride was very effective in causing precipitation from the acetone and ethyl acetate solutions.

EXAMPLE 3

A 35.5 gram (0.1 mole) amount of octadecene-1/maleic anhydride copolymer was hydrolyzed by heating at reflux with about 200 ml of sodium hydroxide solution containing 8.0 grams (0.2 mole) sodium hydroxide. After the reaction mixture cooled to 70° C., 17 ml. concentrated hydrochloric acid (containing 0.2 mole HCl) was added, the mixture cooled to 40° C., vacuum filtered, and the wet filter cake treated with 400 grams acetone to form a solution. Acetone was distilled off to leave 100 ml. solution which was then added to 400 ml 1,2-dichloroethane at 5° C., causing precipitation. The material was filtered and the solids on the filter were washed with a mixture of 40 ml 1,2-dichloroethane and 6 ml acetone. The solids were dried in a vacuum oven, 33.5 grams being obtained. The filtrate was evaporated to dryness under a vacuum to leave 0.9 gram residue.

EXAMPLE 4

A 35.1 gram amount of octadecene-1/maleic anhydride copolymer was heated in 140 ml water containing 1 gram salt and 1 gram surfactant to 65° C. for several hours. The material was filtered, washed in 100 ml water, filtered and air dried two hours to obtain 38 grams product. The product was dissolved in 38 grams acetone at 35° C. (85 ml solution) and poured into 350 ml 1,2-dichloroethane and mixed in a blender at moderate speed for five minutes. The material was filtered, and the solids washed in a solution of 9.5 grams acetone, 85 ml 1,2-dichloroethane filtered and air dried 20 minutes to produce 36 grams material. After an additional 15 minutes air drying on a filter, the weight was 34.5 grams. Distillation of the solvent to dryness left a 3.0 gram residue.

EXAMPLE 5

Samples of several different α-olefin/maleic acid copolymers were obtained by hydrolysis of the corresponding α-olefin/maleic anhydride copolymers, the α-olefins being the $C_{10}$, $C_{14}$, $C_{18}$ and $C_{20}$. The samples were refined by a procedure in which 20 grams of a sample was dissolved in 20 grams acetone at room temperature, and the resulting solution poured into 240 grams of dichloroethane at room temperature, with good mixing, to precipitate the polymer. The materials were filtered, washed with 20 grams of a 12/1 dichloroethane to acetone weight ratio solution, and the product dried and the weight of product and residue from the filtrate determined, with results as follows:

| C-No.: | Product (grams) | Residue (grams) | Total Recovery (grams) | Product % of Total |
|---|---|---|---|---|
| 10 | 16.2 | 0.5 | 16.7 | 97.0 |
| 14 | 16.2 | 0.4 | 16.6 | 97.6 |
| 18 | 16.8 | 1.2 | 18.0 | 93.3 |
| 20 | 15.4 | 1.7 | 17.1 | 90.1 |

Infra-red determinations were made on all product and gave comparable charts, indicating similar polymeric material and anhydride content. A calculation of the $C_{18}$ product showed 11.3% anhydride content. All polymer products had higher anhydride content then the starting maleic acid copolymer samples. Gel permeation chromatography of all products showed higher molecular weight than the starting polymer, while all residues showed low molecular weight components.

EXAMPLE 6

Samples of octadecene-1/maleic acid copolymer were dissolved in a number of solvents, using 50 grams polymer to 50 grams solvent. The solutions were then poured into 600 grams dichloroethane and if precipitation resulted, the solids were filtered, washed with 50 grams dichloroethane, and dried.

Results and polymer recoveries were as follows:

| Solvent | % Recovery |
|---|---|
| ethyl acetate | 87 |
| dimethylformamide | gel |
| dimethylsulfoxide | no precipitate |
| di-isopropyl ether | 89 |
| methyl isobutyl ketone | 88.9 |
| methyl ethyl ketone | 89.6 |
| cyclohexanone | 87.1 |
| xylene | 83.8 |
| acetone | 87.6 |
| ethylene glycol | no solution |
| isopropyl alcohol | no precipitate |
| tetrahydrofuran | 69.6 (semi-gel) |
| toluene | 92.9 |
| chloroform | 97.8 |

The results demonstrate that good recoveries are obtainable with most of the solvents. Gel formation occurs readily in several solvents, e.g. from the dimethylformamide a gel precipitated which would be difficult to separate efficiently in large scale operations. With the tetrahydrofuran, a gel was formed, but addition of 500 grams more dichloroethane lessened the gel characteristics, and a fair amount of product was separated by filtration. From isopropyl alcohol, a gel formed which did not separate on the filter. With dimethyl sulfoxide solvent, the usual amount of dichloroethane did not cause precipitation.

EXAMPLE 7

Solutions of octadecene-1/maleic acid copolymer, 50% by weight, in acetone were prepared, and 2 gram aliquots were added at room temperature to 12 gram samples of selected non-solvents to see whether precipitation was effected. The samples were then cooled to −20° C., observed, and warmed back to room temperature. Results are as follows:

| Non-solvent | Solubility Room Temperature | Solubility −20° C. | Solubility Back to Room Temp. |
|---|---|---|---|
| Methylene Chloride | Soluble | Mushy | Soluble |
| chloropropane | Soluble | " | Soluble |
| 1,2 dichloro-propane | Slightly cloudy | " | Slightly cloudy |
| isooctane | Soluble | " | " |
| cyclohexane | Soluble | " | " |
| methylcyclohexane | Soluble | " | " |
| heptane | Soluble | " | (gel on/standing overnight) |
| dichloroethane | Precipitate | — | Slightly Cloudy |

The superiority of dichloroethane as a precipitating solvent is clearly demonstrated in this test, although some potential for 1,2-dichloropropane is indicated. Similar tests were conducted with these non-solvents by the same procedure at room temperature in other solvents, namely toluene, ethyl acetate, chloroform, and dipentene. The advantage of dichloroethane was again demonstrated, a good precipitation being obtained in every case. With a few exceptions, the polymer remained in solution with the other non-solvents. The 1,2-dichloroethane gave a small precipitate from ethyl acetate and chloroform. (the polymer concentration was 33% in the chloroform solutions). The methylene dichloride gave a cloudy solution with some precipitate from ethyl acetate. Upon standing overnight, the heptane produced a gel from dipentene and a glass from toluene.

The following illustrates a procedure which can be utilized in carrying out the present invention, starting with crude anhydride copolymer.

A 100 lb portion of octadecene-1/maleic anhydride copolymer is hydrolyzed with 200 lbs. water containing 2 lbs. of sodium chloride at 60° C., employing a stirred vessel under nitrogen. The extent of conversion can be monitored by infra red, with the usual time being 18 to 24 hours for 90% conversion. The slurry is cooled to 30° C. and filtered through a filter press, or separated by centrifuge. The filter cake can be dried in a vacuum pan dryer at 45° C. and 20 mm vacuum overnight to 20% water content. As an alternative, the filter cake can be fluidized without partial predrying. The polymer is then slurried with 500 lbs. of 1,2-dichloroethane for three hours at 20°-25° C. The slurry is filtered on a filter press to isolate the polymer, which is then washed twice with 250 lbs. of dichloroethane. The slurry and wash steps can be repeated. A centrifuge can be substituted for the filter press to permit more effective washing. The polymer is then dissolved in 100 lbs. of acetone by stirring at 20°-25° C. for up to one hour. The acetone solution is clarified by passing through an in line filter, and added to a stirred kettle containing 1200 lbs. of 1,2-dichloroethane. The polymer precipitates and low molecular weight fraction (approximately that below 2000 Daltons) remains in solution. The kettle is stirred for one half hour at 20°-25° C. The polymer is isolated by filtration, preferably by centrifuge. The residual dichloroethane is removed in a vacuum tray dryer at 50° C. at 10-20 mm pressure, and product is ground in a mill to break up any lumps prior to rehydrolysis. At this point, anhydride content may be 15-20%. The polymer is rehydrolyzed in 250 lbs. water at 50° C. for 6 hours under nitrogen, with infrared analysis to monitor progress to an anhydride level of less than 10%. This step also removes traces of salt, and dichloroethane and reduces any maleic acid present. The product is then filtered through a filter press or centrifuged, and dried as described above, but controlled to retain 10-15% water to prevent dehydration to the anhydride. The product is then ground twice, first in a hammermill to 20 mesh or smaller, then in a micro-pulverizer. The product can then be packaged in polyethylene-lined drums and stored, preferably at temperatures not over 25° C. The procedure starting with 100 lbs. of the anhydride copolymer will generally produce 95-100 lbs. of the refined acid copolymer having about 10% moisture content.

The polymers utilized in the present invention ordinarily have a fairly broad molecular weight distribution as is typical of polymers formed by free radical polymerization. Typical samples may have weight average ($M_w$) molecular weights around 55,000 to 65,000 and number average molecular weights ($M_n$) around 24,000 to 28,000 Daltons. These molecular weight characterizations, and Mw/Mn which is a measure of heterogenity have some value, but are not specifically designed to measure the amount of low molecular weight, e.g. in the range of up to 1000 or 2000 Mw, which are removed in the present process. Aside from the assumed value of removing such low molecular weight species, there is no concern over the distribution of the molecular weights, or about the presence of particular molecular weights, whether well below Mw 50,000, or far above Mw, 65,000 or 100,000 or so. The polymers are considered effective and suitable for use over broad ranges, even at extremely high molecular weights over a million or more, and particular ranges are given for illustration. Typical polymer has Mw over 50,000 and Mn over 22,000.

The polymers utilized in, and as refined by, the present invention can be characterized by gel permeation chromatography. Highly porous, rigid polystyrene resin gell particles, such as the Styrogel ® brand gel particles, closely packed in tubes, can be used. The transit time of polymer in solution is measured, with the larger molecules exiting faster. For example, in a particular permeation, on product refined as described herein, the bulk of the polymer passed in about 10 to 12 minutes, with a peak at about 10.75 minutes, while the residue obtained from the solvent fractionation (filtrate residue) had a transit time of about 11 to 14 minutes with a fairly broad distribution over this range, and a similar result was obtained from the residue of wash liquids used to wash the solid product.

The polymer utilized herein can have the bulk of residual olefin removed by slurrying with dichloroethane, and may then have less than 0.5% residual monomers, with very little maleic acid, and ordinarily no more than 0.3% by weight of molecules of less than 2000 molecular weight. After refining as described herein, the monomer content will typically be no more than 400 parts per million β-olefin, possibly in the range of 30 to 200 parts per million, no more than 20 parts per million maleic acid, and less than 0.1% by weight of molecules under 2000 molecular weight with none measured under 1000 molecular weight, and it is possible to reach nominal measurements of zero molecules under 2000. The measurements may involve an error of ±10 to 15% in these ranges. In addition to removing monomers and low molecular weight materials, the procedures herein also unavoidably remove some higher molecular weight or anhydride materials, but the losses are in acceptable ranges.

In the preparation of refined polymer in accord with the present invention, it is desirable that the product be ground or otherwise reduced to fine particle size in order to have a product well suited to pharmaceutical use. The polymer can be ground in a Fitz mill to a size of 20 mesh or smaller, and then further reduced as by air milling in a micro-pulverizer or the like to have the majority of the final product in the range of 200 to 325 mesh (0.074-0.043 mm). It is preferred to air mill the material to the extent that 70% or even 95% or so of the product passes a 325 mesh and is generally of much smaller particle size than 0.043 mm.

The use of the material in small particle size form has the advantage of minimizing "graininess" feel upon oral administration. Moreover there is evidence that the small particle size contributes markedy to effectiveness of the material. The material is essentially a non-systemic agent the effect of which may involve some surface phenomenon. The polymeric products described herein are useful for controlling blood cholesterol levels, regardless of the mode of action, but the foregoing provides an explanation of the effect of particle size.

In order to retain the advantages of the fine particle size product as described herein, it is not necessary to administer the material as a fine powder. The material can be pressed into tablets or other dosage forms or otherwise formed into a composite in which the particles retain their identity to a sufficient extent to minimize graininess and to readily desintegrate so as to have the advantage of the ultimate small particle sizes. Of course, the refining procedures herein are advantageous in removing undesired materials regardless of whether the product is used in very finely divided form, and the product can be utilized in any form suitable for oral administration including usual unit dosage forms for oral administration of pharmaceuticals, with the polymer alone or with excipients, and the polymers can also be incorporated into various foods, or included in liquid formulations.

The process of the present invention produces pharmaceutical grade higher olefin/maleic acid copolymer with no more than 20% anhydride content, no more than 400 parts per million α-olefin, no more than 20 parts per million maleic acid, less than 0.1% by weight of molecules less than 2000 molcular weight, and preferably with particle sizes with at least 70% of maximum no greater than 0.043 mm. Since the polymer results from a free radical polymerization, it has the heterogeneous molecular weight distribution typical thereof, except for removal of lower molecular weight materials.

In carrying out the process of the present invention, particularly in large scale operations, it may be desirable to employ particular handling and separation procedures found to be advantageous by applicants' associates, Robert P. Bell and Lawrence E. Stout, Jr. . Slurries or solutions of polymers as described herein are subject to possible gel formation upon removal of solvent such as acetone therefrom, and applicants' associates have found that gel formation is influenced by temperature, time, shear and pressure, and that gel formation can be avoided by properly limiting the foregoing variables so that their combined effect does not cause gellation. For convenient and efficient handling, particularly in large scale operations, it will be appropriate to subject the polymer solutions or slurries to various forces, as by pumping from one location to another and use of pressure in a filter press or centrifuge for filtration. The use of low shear pumps, such as diaphragm or piston pumps is desirable to limit shear, and pressures in a centrifuge operating at basket forces up to 200 G's may be appropriate, if the temperature is sufficiently controlled, as around 0° C. For example, a laboratory scale centrifuge, 5 inch diameter, operating at 1700 rpm. The low temperatures can be obtained by mixing an acetone solution of the polymer into dichloroethane which has been cooled to the desired temperature. The time the resulting mixture is maintained at a particular temperature is also influential, and with large volumes of materials which may require a number of hours for filtration, it is desirable to have conditions which permit such times. However, procedures can be used which shorten the time from precipitation to filtration, as use of a static in-line mixer to mix incremental quantities of acetone polymer solution and dichloroethane on a continuous basis, and to filter immediately. For example applicants associates have found that, on a laboratory scale the solution and dichloroethane can run from a T joint through a Kenec mixer which is ⅜ inch diameter and 10 inches long and contains fluted vanes or baffles for mixing, using such flow rates as 20 ml per minute. Avoiding or lessening gel formation contributes to the efficiency of the operation by avoiding unduly long or difficult filtrations.

What is claimed is:

1. A method of refining α-olefin/maleic acid copolymer in which the olefin is a higher olefin, which comprises selectively precipitating such copolymer from solution with dichloroethane.

2. The method of claim 1 in which said solution comprises octadecene-1/maleic acid copolymer.

3. The method of claim 1 in which said solution comprises said copolymer and acetone.

4. The method of claim 1 in which the dichloroethane is employed in about 3 to about 12 weight parts per weight part of solution.

5. The method of claim 4 in which the solution comprises about 30 l to about 60% by weight of copolymer.

6. The method of claim 1 in which the olefin has about 10 to about 22 carbon atoms and the solution is filtered prior to precipitating such polymer.

7. A method of preparing a refined higher αolefin/maleic acid copolymer which comprises hydrolyzing a higher α-olefin/maleic anhydride copolymer, dissolving the hydrolyzed copolymer in a solvent, precipitating the polymer from the resulting solution with dichloroethane, and separating the polymer from the dichloroethane.

8. The method of claim 7 in which the maleic anhydride copolymer is hydrolyzed in aqueous sodium chloride solution.

9. The method of claim 7 in which the polymer is separated by filtration.

10. The process of claim 7 in which the polymer is separated by centrifugation.

11. The method of claim 8 in which the polymer after separation is treated with water, separated therefrom, and dried.

12. The method of claim 11 in which the drying is controlled to prevent dehydration to the anhydride.

13. The method of refining higher α-olefin/maleic acid copolymer which comprises providing such copolymer in solid-liquid contact with dichloroethane, and separating the solid copolymer from the liquid dichloroethane containing dissolved materials which had been present in the copolymer material.

14. The method of claim 13 in which the copolymer in finely divided form is slurried with the dichloroethane prior to separation.

15. The method of claim 13 in which the copolymer is washed with dichloroethane.

16. The method of claim 13 in which the copolymer and dichloroethane are separated by filtration.

17. A refined pharmaceutical grade higher α-olefin/maleic acid copolymer of high molecular weight with heterogeneous molecular weight distribution characterized by the low amount present of low molecular weight polymer removable by functional precipitation from solution and less than 0.1% of molecules of less than 2000 molecular weight and no more than 400 parts per million of α-olefin or maleic acid content.

18. The polymer of claim 17 in which the α-olefin is octadecene-1.

19. The polymer of claim 17 in which the copolymer has a particle size in which at least 70% of particles have a maximum dimension of 0.043 mm.

* * * * *